US011266299B2

(12) United States Patent
Papay

(10) Patent No.: US 11,266,299 B2
(45) Date of Patent: Mar. 8, 2022

(54) ENDOSCOPE FOR TISSUE DISSECTION AND VISUALIZATION

(71) Applicant: THE CLEVELAND CLINIC FOUNDATION, Cleveland, OH (US)

(72) Inventor: Francis A. Papay, Westlake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 222 days.

(21) Appl. No.: 16/220,143

(22) Filed: Dec. 14, 2018

(65) Prior Publication Data
US 2019/0380561 A1 Dec. 19, 2019

Related U.S. Application Data

(63) Continuation of application No. 14/480,935, filed on Sep. 9, 2014, now abandoned.
(Continued)

(51) Int. Cl.
A61B 1/00 (2006.01)
A61B 1/012 (2006.01)
(Continued)

(52) U.S. Cl.
CPC ...... *A61B 1/00082* (2013.01); *A61B 1/00087* (2013.01); *A61B 1/00165* (2013.01);
(Continued)

(58) Field of Classification Search
CPC ............ A61B 1/00082; A61B 1/00087; A61B 1/00165; A61B 1/012; A61B 1/0684; A61B 1/07
See application file for complete search history.

(56) References Cited

U.S. PATENT DOCUMENTS 4,784,133 A 11/1988 Mackin
5,762,604 A 6/1998 Kieturakis
(Continued)

FOREIGN PATENT DOCUMENTS

EP 1731082 A1 12/2006
WO 2003/101287 A2 12/2003
WO 2009/029639 A1 3/2009

OTHER PUBLICATIONS

PCT International Search Report and Written Opinion for corresponding PCT Application Serial No. PCT/US2014/054684, dated Dec. 15, 2014, pp. 1-13.
(Continued)

*Primary Examiner* — Aaron B Fairchild
(74) *Attorney, Agent, or Firm* — Tarolli, Sundheim, Covell & Tummino LLP

(57) ABSTRACT

One aspect of the present disclosure relates to an endoscope for facilitating a medical procedure by creating an anatomic space in or adjacent a target bodily tissue to be imaged. The endoscope can comprise a flexible, elongate tubular member defining a central lumen and an expandable dissecting member coupled to a distal end of the tubular member. The tubular member can further include at least one imaging channel extending longitudinally therethrough. The at least one imaging channel can include a visualization system for conveying an image from the distal end of the tubular member to a user. The expandable dissecting member can define a channel in fluid communication with the central lumen of the tubular member. The expandable dissecting member can extend beyond the distal end of the tubular member.

10 Claims, 5 Drawing Sheets

Related U.S. Application Data

(60) Provisional application No. 61/875,413, filed on Sep. 9, 2013.

(51) Int. Cl.
    *A61B 1/06*     (2006.01)
    *A61B 1/07*     (2006.01)
    *A61B 1/32*     (2006.01)

(52) U.S. Cl.
    CPC ............ *A61B 1/012* (2013.01); *A61B 1/0684* (2013.01); *A61B 1/07* (2013.01); *A61B 1/32* (2013.01)

(56) References Cited

U.S. PATENT DOCUMENTS

| | | |
|---|---|---|
| 6,306,081 B1 | 10/2001 | Ishikawa et al. |
| 7,534,204 B2 | 5/2009 | Starksen et al. |
| 2004/0097788 A1 | 5/2004 | Mourlas et al. |
| 2005/0197530 A1 | 9/2005 | Wallace et al. |
| 2006/0264708 A1 | 11/2006 | Horne, Jr. |
| 2007/0213584 A1 | 9/2007 | Kim et al. |
| 2009/0318797 A1 | 12/2009 | Hadani |
| 2011/0301417 A1 | 12/2011 | Mourlas et al. |
| 2012/0209286 A1 | 8/2012 | Papay et al. |

OTHER PUBLICATIONS

Olympus America "Balloon Control Unit (OBCU)", https://medical.olympusamerica.com/products/control/balloon-control-unit-obcu last access Oct. 13, 2021.

Olympus America "EVIS EXERA II (SIF-Q180)", https://medical.olympusamerica.com/products/enteroscope/evis-exera-ii-sif-q180 last access Oct. 13, 2021.

Applied Medical "Kii Dissecting Balloon Access Systems", https://www.appliedmedical.com/Products/Kii/DissectingBalloons last access Oct. 13, 2021.

Medtronic US "Spacemaker™ Pro Access & Dissector System", https://www.medtronic.com/covidien/en-us/products/hernia-repair/spacemaker-pro-access-and-dissector-system.html last access Oct. 13, 2021.

ENDOSCOPE FOR TISSUE DISSECTION AND VISUALIZATION

RELATED APPLICATION

This application is a Continuation of U.S. patent application Ser. No. 14/480,935, filed Sep. 9, 2014, which claims the benefit of U.S. Provisional Patent Application Ser. No. 61/875,413, filed Sep. 9, 2013, the entirety of both are incorporated herein by reference for all purposes.

TECHNICAL FIELD

The present disclosure relates generally to a surgical instrument and method for visualizing a target bodily tissue and, more particularly, to an endoscope for tissue dissection to provide an adequate depth of field for fiberoptic viewing.

BACKGROUND

Surgeons in the past have used blunt-tipped instruments as well as balloons in connection with endoscopic surgery to dissect tissue and develop a working space in the interior of the body. Typically, the development of such a working space is done blindly or under endoscopic viewing only if at least one accessory port or accessway is established. To perform a surgery in such a working space, the working space is maintained by insufflation with carbon dioxide gas, which provides room for viewing with an endoscope as well as room for manipulating accessory instruments. To introduce such accessory instruments into the working space, additional incisions typically are made by plunging a sharp-tipped trocar through the distended body wall overlying the insufflated working space.

It has been found that it may be undesirable to dissect accessways and anatomic spaces blindly. It also has been found that it may be difficult to make additional incisions into a dissected anatomic space, particularly if of limited volume or if overlying delicate anatomic structures. Additionally, it has been found that insufflation of a working space with carbon dioxide causes tissue emphysema, which may be undesirable for particular patients because of excessive carbon dioxide absorption into the blood, thus making a minimally invasive endoscopic approach unsuitable.

SUMMARY

The present disclosure relates generally to a surgical instrument and method for visualizing a target bodily tissue and, more particularly, to an endoscope for tissue dissection to provide an adequate depth of field for fiberoptic viewing.

One aspect of the present disclosure relates to an endoscope for facilitating a medical procedure by creating an anatomic space in or adjacent a target bodily tissue to be imaged. The endoscope can comprise a flexible, elongate tubular member defining a central lumen and an expandable dissecting member coupled to a distal end of the tubular member. The tubular member can further include at least one imaging channel extending longitudinally therethrough. The at least one imaging channel can include a visualization system for conveying an image from the distal end of the tubular member to a user. The expandable dissecting member can define a channel in fluid communication with the central lumen of the tubular member. The expandable dissecting member can extend beyond the distal end of the tubular member Another aspect of the present disclosure relates to an endoscope for facilitating a medical procedure by creating an anatomic space in or adjacent a target bodily tissue to be imaged. The endoscope can comprise a flexible, elongate tubular member and an expandable dissecting member coupled to a distal end of the tubular member. The tubular member can further include at least one imaging channel extending longitudinally therethrough. The at least one imaging channel can include a visualization system for conveying an image from the distal end of the tubular member to a user. The expandable dissecting member can completely envelope, and extend beyond, the distal end of the tubular member.

Another aspect of the present disclosure relates to a method for visualizing a target bodily tissue of a patient during a medical procedure. One step of method can include providing an endoscope comprising a flexible, elongate tubular member and an expandable dissecting member coupled to a distal end thereof. The tubular member can further include a visualization system for conveying an image from the distal end of the tubular member to a user. The endoscope can be inserted into the patient with the expandable dissecting member in a deflated configuration. Next, the distal end of the tubular member can be advanced towards the target tissue. The dissecting member can then be inflated to create an anatomic space in or adjacent the target tissue. The visualization system can be operated to convey an image of the target tissue from the distal end of the tubular member to the user.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1A:
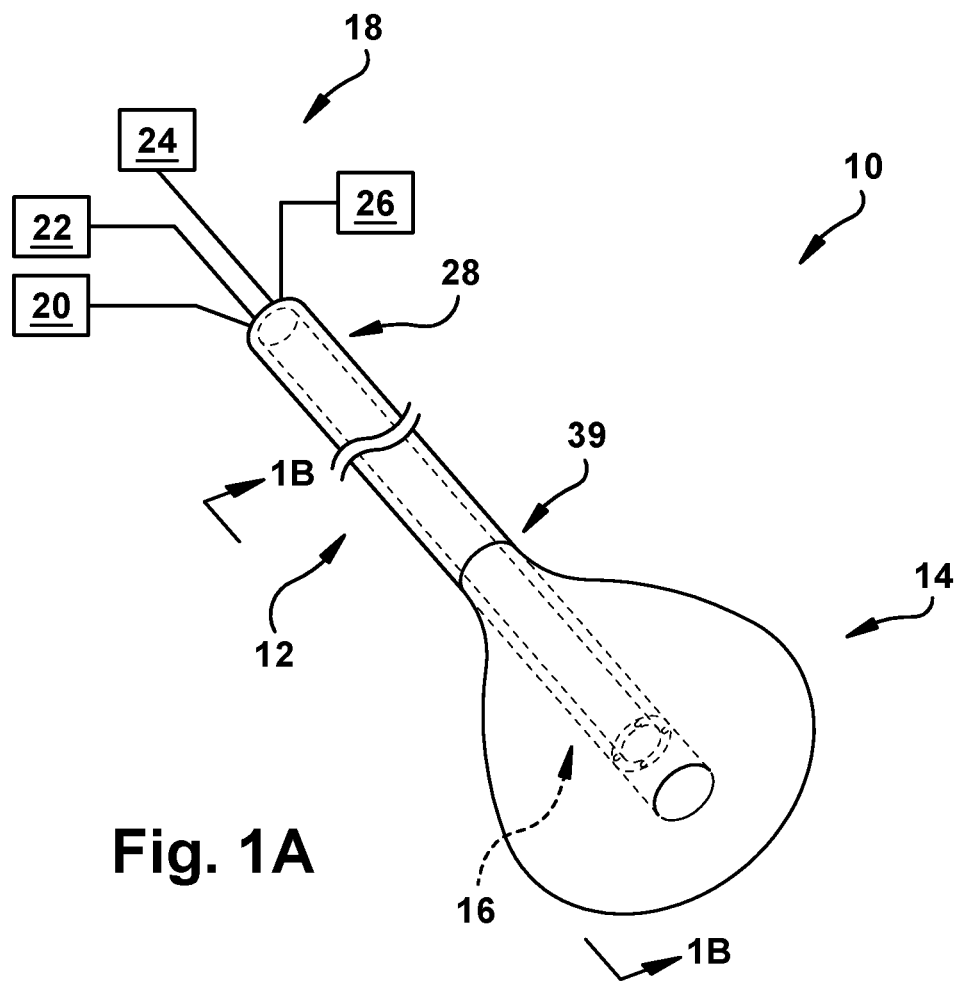
FIG. 1A is a perspective view of an endoscope and associated imaging components constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "endoscope" can refer to any type of invasive instrument, flexible or rigid, having scope features. These include, but are not limited to, microendoscopes, colonoscopes, gastroscopes, laparoscopes and rectoscopes.

As used herein, the term "microendoscope" can refer to an endoscope having a small diameter, such as less than about 3 mm.

Overview

Figure 1B:
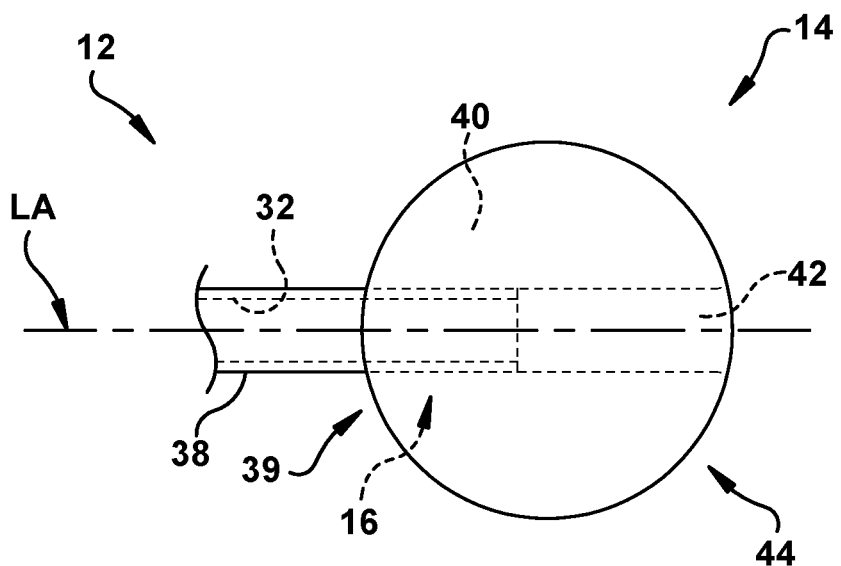
FIG. 1B is a cross-sectional view taken along Line 1B-1B in FIG. 1A.
Figure 1C:
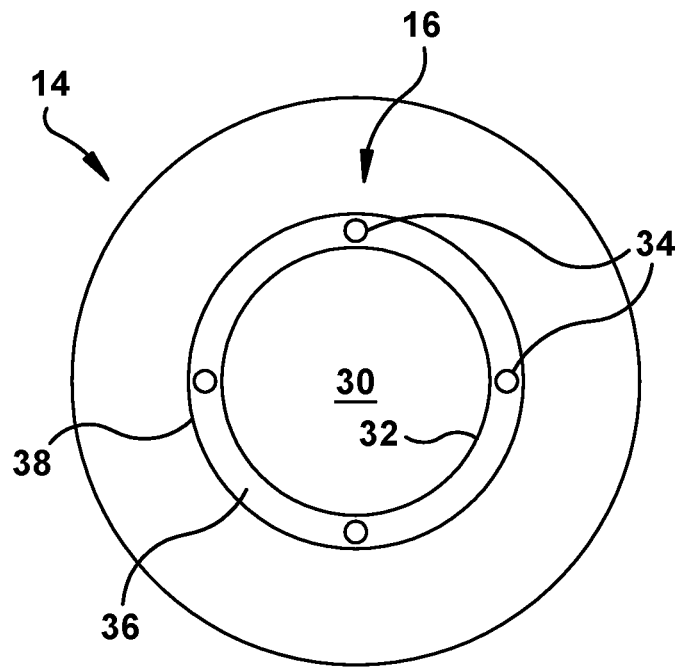
FIG. 1C is a schematic illustration showing a front view of the distal end of the endoscope in FIGS. 1A-B.

The present disclosure relates generally to a surgical instrument and method for visualizing a target bodily tissue and, more particularly, to an endoscope for tissue dissection to provide an adequate depth of field for fiberoptic viewing. As illustrated in FIGS. 1A-C, one aspect of the present disclosure can include an endoscope 10 for facilitating a medical procedure by creating an anatomic space in or adjacent a target bodily tissue to be imaged. The endoscope 10 of the present disclosure is a low-cost, flexible fiberoptic scope that can be used to visualize or image a variety of target bodily tissues during any number of minimally invasive or less invasive medical procedures. The endoscope 10 can be used alone or in conjunction with other medical devices, depending upon its intended application. For example, the endoscope 10 can be used as part of, or in conjunction with, an endotracheal intubation tube (not shown) or laryngeal mask (not shown) to permit an anesthesiologist to scope, intubate, and monitor during anesthesia and intubation of a patient's trans-laryngeal and tracheal airway. Other applications of the endoscope 10, as well as advantages of the present disclosure, are discussed in more detail below.

Certain aspects of the present disclosure can facilitate transvascular, minimally invasive, and other "less invasive" medical procedures by providing direct visualization of a target bodily tissue. The phrase "less invasive" can mean any procedure that is less invasive than traditional, large-incision open medical or surgical procedures. For example, a less invasive procedure may be an open surgical procedure involving one or more smaller incisions, a transvascular or percutaneous procedure, a transvascular procedure via cutdown, a laparoscopic procedure, or the like. Generally, any medical procedure in which a goal is to minimize or reduce invasiveness to the patient may be considered less invasive. Although the terms "less invasive" and "minimally invasive" may sometimes be used interchangeably in this application, neither these nor other descriptive terms should be interpreted to limit the scope of the present disclosure. Generally, the present disclosure may be used in performing or enhancing any suitable medical procedure, such as laparoscopic or other endoscopic procedures on any part of the body.

Endoscopes

One aspect of the present disclosure includes an endoscope 10 for facilitating a medical procedure by creating an anatomic space in or adjacent a target bodily tissue to be imaged. As shown in FIG. 1A, the endoscope 10 can comprise a flexible, elongate tubular member 12 and an expandable dissecting member 14 coupled to a distal end 16 of the elongate tubular member. In one example, the endoscope 10 can be a microendoscope.

To facilitate operation of the endoscope 10 during a medical procedure, various imaging components 18 may be associated with the endoscope. Examples of such imaging components 18, whose operation is discussed in more detail below, can include a vacuum or suction source 20, a fluid source 22, a processor 24 or visualization control system, and a display 26 or image viewer. Although the endoscope 10 is described herein as including an expandable dissecting member 14, it will be appreciated that certain aspects of the present disclosure may include an endoscope that is free of an expandable dissecting member. In such instances, the endoscope 10 may be associated with one or more medical devices, such as an endotracheal intubation tube or laryngeal mask, or, alternatively, the endoscope may be used as a standalone device.

In another aspect, the elongate tubular member 12 can include a proximal end 28, a distal end 16 having a size and shape for insertion into a patient's body, and a central lumen 30 (FIG. 1B) extending between the proximal and distal ends. A longitudinal axis LA can extend parallel, or substantially parallel to, the central lumen 30. In some instances, the central lumen 30 can be defined by an inner surface 32 of the elongate tubular member 12. It will be appreciated that the elongate tubular member 12 can include two or more lumens extending longitudinally therethrough or, alternatively, that the elongate tubular member may be a solid structure that is free of any longitudinally-extending lumens. The elongate tubular member 12 (FIG. 1A) may be substantially flexible, semi-rigid, and/or rigid along its length, and may be formed from a variety of materials, including plastic, metal, and/or composite materials. For example, the elongate tubular member 12 may be substantially flexible at the distal end to facilitate advancement through tortuous anatomy, and/or may be semi-rigid or rigid at the proximal end 28 to enhance pushability of the endoscope 10 without substantial risk of buckling or kinking.

In some instances, the elongate tubular member 12 can be steerable, e.g., the distal end 16 may be controllably deflected transversely relative to the longitudinal axis LA. In such instances, a single pullwire (not shown) or other steering element may be provided (e.g., within a lumen) for steering the distal end 16 in one transverse plane (thereby providing one degree of freedom). Alternatively, two pullwires may be provided for steering the distal end 16 in two orthogonal planes (thereby providing two degrees of freedom). The pullwire(s) can include a cable, wire, band, or the like, that may be slidably disposed within a lumen. The pullwire(s) may be attached or otherwise fixed relative to the elongate tubular member 12 at a location adjacent the distal end 16, e.g., offset radially outwardly from the longitudinal axis LA. Thus, when a pullwire is pulled proximally (e.g., from the proximal end 28 of the elongate tubular member 12) a bending force may be applied to the distal end 16, causing the distal end to bend transversely relative to the longitudinal axis LA.

The elongate tubular member 12 may also include a handle (not shown) or other control mechanism coupled to or otherwise provided on the proximal end 28 thereof. In such instances, the handle can have a shape, size, and/or contour to facilitate tactile manipulation the elongate tubular member 12 during use. In some instances, the handle can include one or more steering controls that may be actuated to steer the distal end 16 of the elongate tubular member 12. For example, a dial (not shown) may be provided that may be coupled to a pullwire. The dial may be rotated to apply a proximal force on the pullwire, thereby bending the distal end 16 of the elongate tubular member 12. The handle may also include ports and/or other connections for connecting one or more of the imaging components to the elongate tubular member 12.

It will be appreciated that any known connector(s) may be provided for permanently or temporarily connecting components (e.g., imaging components 18) to the elongate tubular member 12. For example, a Luer lock connector (not shown) may be used to connect tubing or other fluid-conveying components to the elongate tubular member 12. A syringe (not shown) or other source of fluid, e.g., including saline, carbon dioxide, nitrogen, or air, may be connected via tubing (not shown) to the elongate tubular member 12. In such instances, the syringe may also provide a source of vacuum for deflating the expandable dissecting member 14. Another source of fluid (not shown), e.g., saline, and/or a therapeutic or diagnostic agent, may be connected via tubing (not shown) to the elongate tubular member 12 for delivering fluid beyond the distal end 16 thereof.

In another aspect, the elongate tubular member 12 can include at least one imaging channel 34 (FIG. 1C) that extends longitudinally therethrough. In some instances, the imaging channel 34 can be embedded within the wall 36 of the elongate tubular member 12, which is defined by the inner surface 32 and an outer surface 38 thereof. Although not shown in detail, the imaging channel 34 can include oppositely disposed openings that are concentric with the proximal and distal ends 28 and 16 of the elongate tubular member 12. The imaging channel 34 can be circumferentially disposed about the central lumen 30 of the elongate tubular member 12. The imaging channel 34 can have a circular cross-sectional profile; however, it will be appreciated that other cross-sectional profiles are possible (e.g., ovoid, square, rectangular, etc.). Where the elongate tubular member 12 includes two or more imaging channels 34, the imaging channels can have the same or different cross-sectional profiles and/or the same or different dimensions (e.g., radii).

It will be appreciated that the elongate tubular member 12 can include other channels extending therethrough. In one example, the elongate tubular member 12 can include an inflation channel (not shown) for delivering an inflation medium to the expandable dissecting member 14. In such instances, the inflation channel can be embedded within the wall 36, beginning at the proximal end 28 of the elongate tubular member 12 and extending distally until a distal opening thereof is in fluid communication with an interior chamber 40 of the expandable dissecting member 14. In another example, the elongate tubular member 12 can include a working channel (not shown) for positioning or delivering one or more instruments (not shown) to a target bodily tissue. Any suitable instrument(s) may be passed through the working channel, such as a surgical clip applier, an ablation device, a suturing device, and the like.

The imaging channel 34 can include a visualization system (not shown in detail) for conveying an image from the distal end 16 of the elongate tubular member 12 to a user. Generally, the visualization system can include any one or combination of imaging devices that enable direct visualization of a target bodily tissue during use of the endoscope 10. In one example, the visualization system can include an imaging element (not shown) and a lighting element (not shown) disposed within first and second imaging channels, respectively. In some instances, the imaging element can comprise an optical fiber and include another image capturing element (e.g., at its distal end), such as a charge-coupled-device (CCD), CMOS, infrared imaging chip and/or other device to capture, digitize, and/or otherwise convert images into electrical signals that may be transferred to a processor 24 and/or display 26. In some instances, the imaging element can comprise a lens, filter, mirror, or other structure configured to control the field of view or focal length thereof. The utilization of an imaging element located at the distal end 16 of the elongate tubular member 12 for purposes of visualizing objects from a point of interest is referred to herein as "direct visualization". In other words, "direct visualization" can refer to placing an imaging "eye" proximate to a target bodily tissue.

In other instances, the lighting element can be operably paired with the imaging element to provide illumination or radiation appropriate for capturing images of a target bodily tissue. Where the imaging element comprises an optical fiber, for example, the lighting element can include an emitter of light, such as a small light bulb, a light-emitting diode, an incandescent light source, or end of another optical fiber. The visualization system, including the imaging and lighting elements, can be coupled (e.g., by a cable) to one or more electronic components for processing and/or displaying images of the target bodily tissue. Examples of such electronic components can include computers or other display or capture devices, such as a laptop computer, handheld or PDA devices, a computer terminal, a LCD display, standard video monitor, and the like, to display and/or store the images acquired from the visualization system. Optionally, the computer (or other capture device) may provide electrical power to the visualization system.

In another aspect, the elongate tubular member 12 can include an expandable dissecting member 14 coupled to the distal end 16 thereof. As discussed in more detail below, the expandable dissecting member 14 can be used to dissect tissue along an anatomic plane under direct visualization. Use of the expandable dissecting member 14 can provide a dissected optical cavity or anatomic space in or adjacent a target bodily tissue to provide adequate depth of field for endoscope viewing by generally applying forces perpendicular to tissue being treated. Consequently, use of the expandable dissecting member 14 during a medical procedure not only provides adequate depth of field, but also removes the need for insufflation with carbon dioxide, which can pose a health hazard to the patient.

The dissecting member 14 may be expandable from a contracted or deflated condition (not shown) to an enlarged or expanded condition when an inflation fluid is introduced into the interior chamber 40 of the dissecting member. For example, a substantially transparent inflation fluid (e.g., saline, carbon dioxide, nitrogen, air, and the like) can be delivered through an inflation channel of the elongate tubular member 12 into the interior chamber 40 of the expandable dissecting member 14. As used herein, the term "transparent" can refer to any material and/or fluid that may permit sufficient light to pass therethrough in order to identify or otherwise visualize bodily tissues or structures through the material and/or fluid. The term "light" can refer to light radiation within the visible spectrum, but may also include other spectra, such as infrared or ultraviolet light. In some instances, the expandable dissecting member 14 can be permanently affixed on or near the distal end 16 of the tubular elongate member 12. For example, a proximal end 39 of the expandable dissecting member 14 can be affixed to the outer surface 38 of the elongate tubular member 12 using an adhesive, heating, sonic welding, an interference fit, and/or an outer sleeve (not shown).

In one example, the expandable dissecting member 14 can comprise a compliant balloon. In such instances, the expandable dissecting member 14 can be made of compliant and/or elastomeric materials, such as silicone, latex, isoprene and chronoprene. In another example, the expandable dissecting member 14 can comprise a non-compliant balloon and be formed, for instance, from a substantially non-compliant material, such as polytetrafluoroethylene, expanded polytetrafluoroethylene, fluorinated ethylenepropylene, polyethylene teraphathalate, urethane, olefins, and/or polyethylene, such that the expandable dissecting member may expand to a predetermined shape when fully inflated. In such instances, the expandable dissecting member 14 may be sufficiently non-compliant to displace tissue and facilitate creation of an anatomic space in or adjacent a target bodily tissue.

In the expanded or enlarged condition, the dissecting member 14 can have a generally annular shape and define a channel 42 (FIG. 1B) that is in fluid communication with the central lumen 30 of the elongate tubular member 12. The term "fluid communication" can refer to a pathway that allows the passing of a fluid and/or light and/or an instrument between the central lumen 30 of the elongate tubular member 12 and the channel 42 of the dissecting member 14. In one example, a distal end portion 44 of the expandable dissecting member 14 can have a toroidal or "donut" shape such that the distal end portion encircles, and overhangs, the distal end 16 of the elongate tubular member 12. In such instances, the toroidal distal end portion 44 of the expandable dissecting member 14 can create a circumferential channel 42 or lumen through which a target bodily tissue can be directly visualized, a fluid can be delivered or aspirated, and/or an instrument can be delivered. In this configuration, the distal end portion 44 of the dissecting member 14 can form a concave surface out of which a field of view of the visualization system extends distally.

Figure 2:
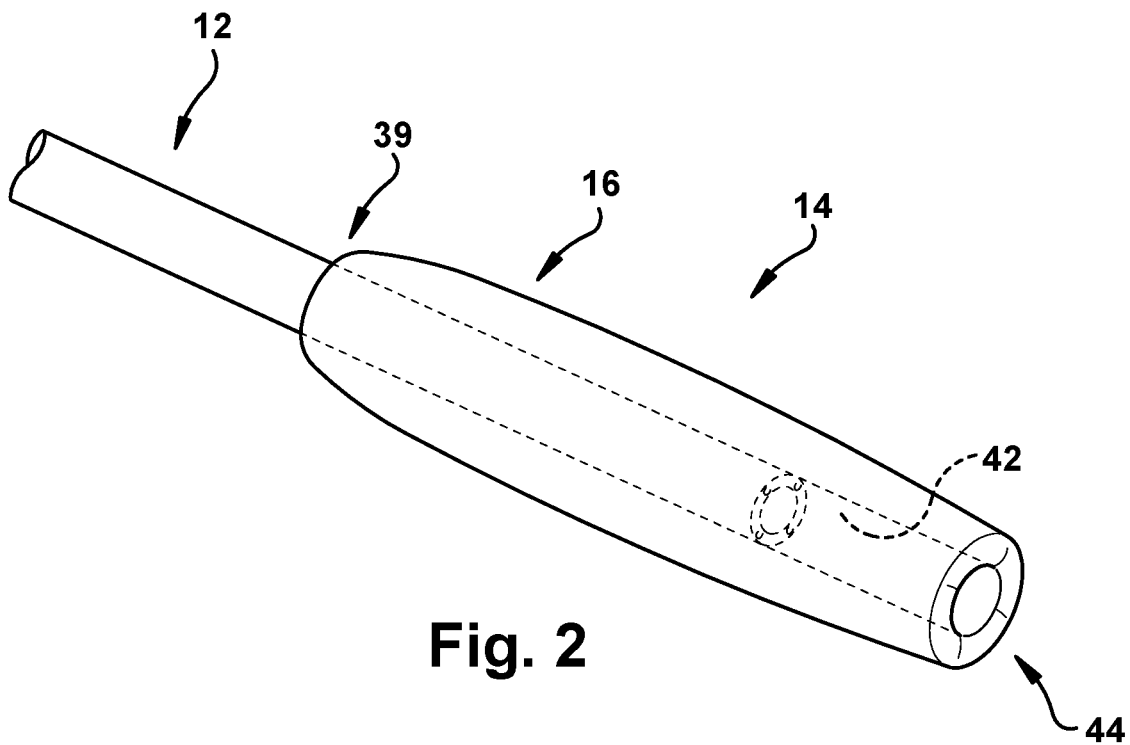
FIG. 2 is a perspective view showing an alternative construction of an expandable dissecting member comprising the endoscope in FIGS. 1A-C.

The distal end 16 of the elongate tubular member 12 can be axially spaced apart from an opening of the channel 42 such that the distal end is not flush or concentric with the opening. Depending upon the configuration of the expandable dissecting member 14, it will be appreciated that the field of view of the visualization system may not include portions of the dissecting member. It will also be appreciated that the expandable dissecting member 14 can have a variety of different shapes when inflated, such as a cylindrical or "hot dog bun" shape (FIG. 2).

Advantageously, the presence of the channel 42 permits visualization of an anatomical tissue or space abutting the distal end portion 44 of the dissecting member 14. This would not be possible if the distal end 16 of the elongate tubular member 12 were flush or concentric with the distal end portion 44 because the imaging surface would be pressed against the tissue, thus removing adequate depth of field for endoscopic viewing. The channel 42 thus makes the endoscope 10 extremely versatile and useful in highly confined anatomical regions where excessive endoscope movement and dissection is not possible.

Figure 3A:
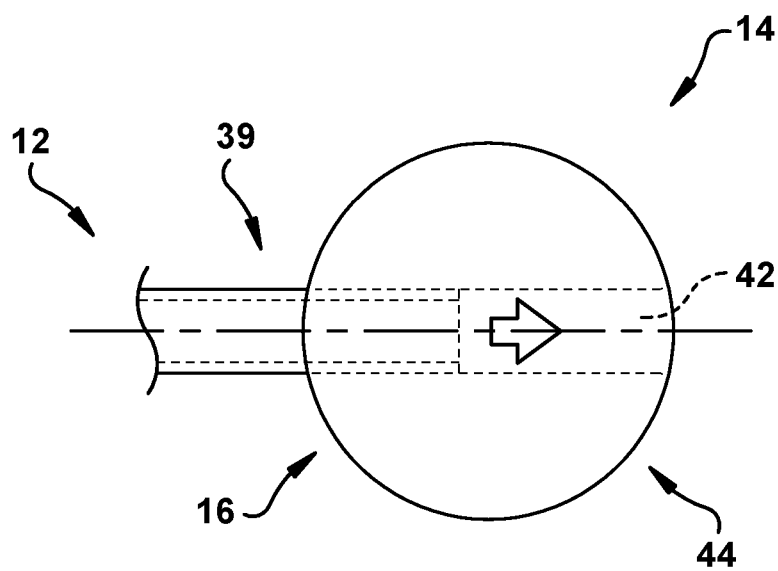
FIGS. 3A-B are cross-sectional views similar to FIG. 1B showing operation of a translation mechanism according to another aspect of the present disclosure.
Figure 3B:
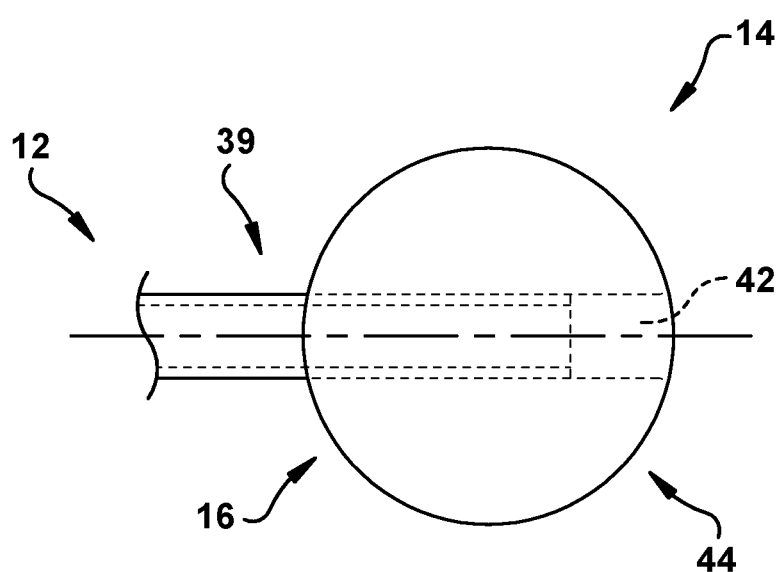

In another aspect, the endoscope 10 can additionally or optionally include a translation mechanism (not shown in detail) configured to permit selective translation of a portion of the elongate tubular member 12 through the channel 42 defined by the expandable dissecting member 14. As shown in FIGS. 3A-B, the translation mechanism allows a user to advance or retract the elongate tubular member 12 in a longitudinal direction (indicated by arrow) relative to the expandable dissecting member 14. In doing so, the dimensions of the channel 42 (e.g., length and volume) can be increased or decreased for different purposes. For example, the length of the channel 42 can be increased by advancing the elongate tubular member 12 in a proximal direction to create a narrower field of view. Alternatively, the length of the channel 42 can be decreased by advancing the elongate tubular member 12 in a distal direction to increase the field of view.

Figure 4A:
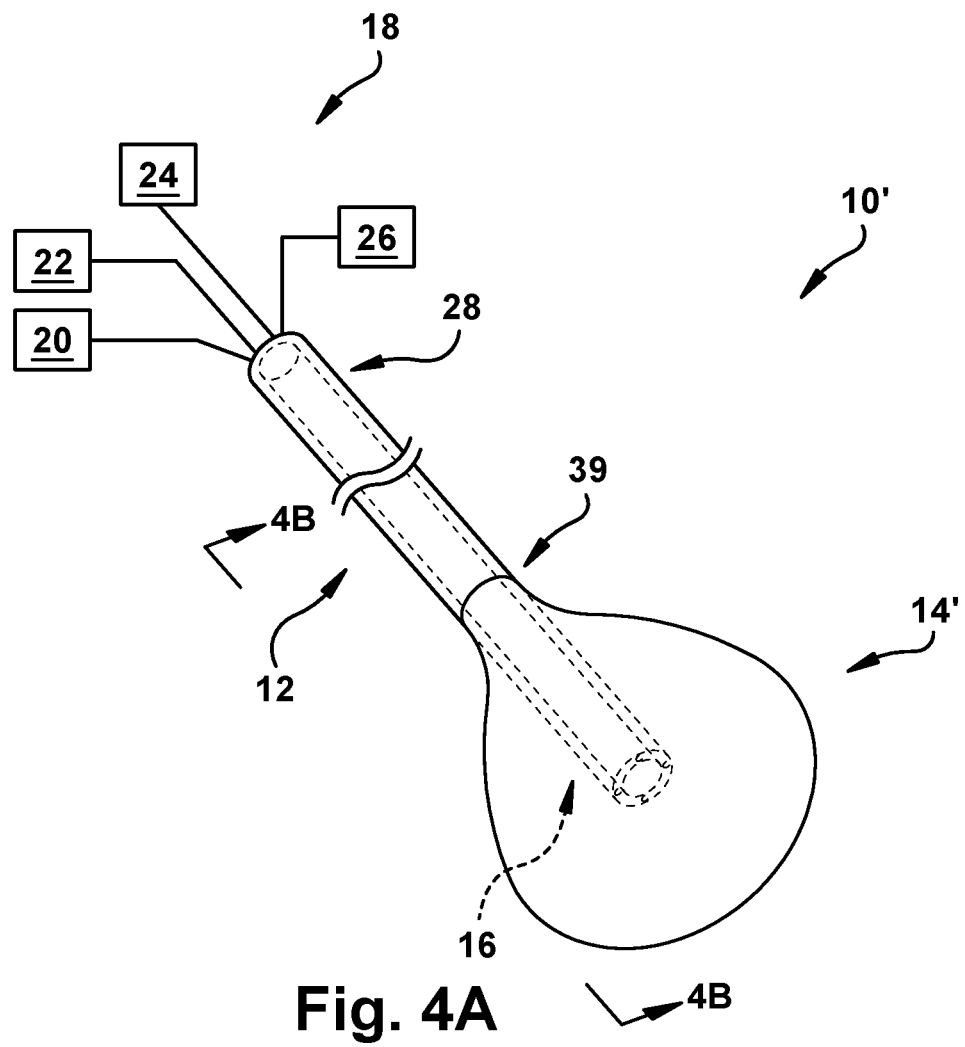
FIG. 4A is a perspective view showing an alternative configuration of the endoscope in FIGS. 1A-C.
Figure 4B:
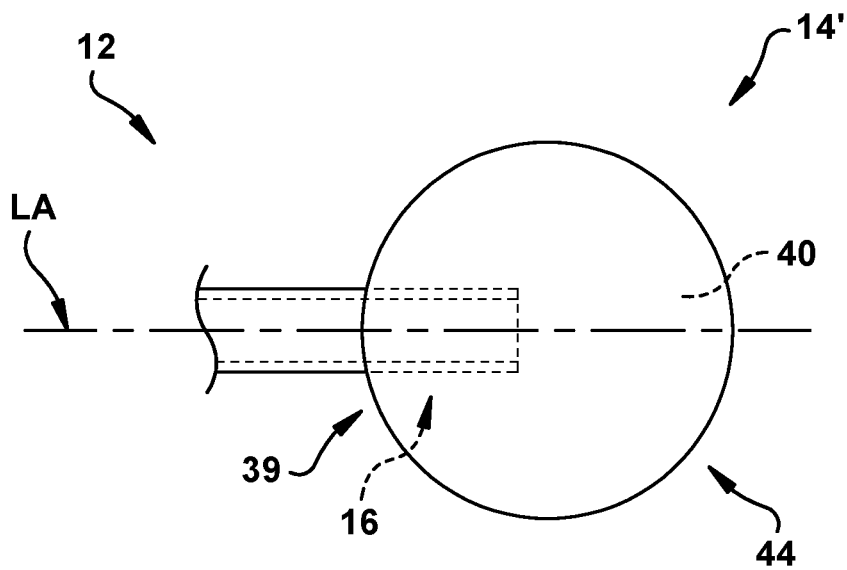
FIG. 4B a cross-sectional view taken along Line 4B-4B in FIG. 4A.

An alternative construction of the endoscope 10 is shown in FIGS. 4A-B. The endoscope 10' in FIGS. 4A-B can be identically constructed as the endoscope 10 in FIGS. 1A-C, except that the expandable dissecting member 14' of the endoscope 10' is configured to completely envelop, and extend beyond, the distal end 16 of the elongate tubular member 12 (e.g., when the dissecting member is in its expanded or enlarged condition). In other words, the expandable dissecting member 14' does not include a channel 42 that directly contacts, or is in fluid communication with, a portion of the elongate tubular member 12 (e.g., the central lumen 30). In this configuration, the expandable dissecting member 14' can be made from one or more substantially transparent materials (such as those discussed above), and can be selectively filled with a substantially transparent inflation medium (also discussed above). Also in this configuration, the elongate tubular member 12 may not include a central lumen 30 and, instead, only include a visualization system as described above. In one example, the endoscope 10' can comprise a microendoscope.

Figure 5:
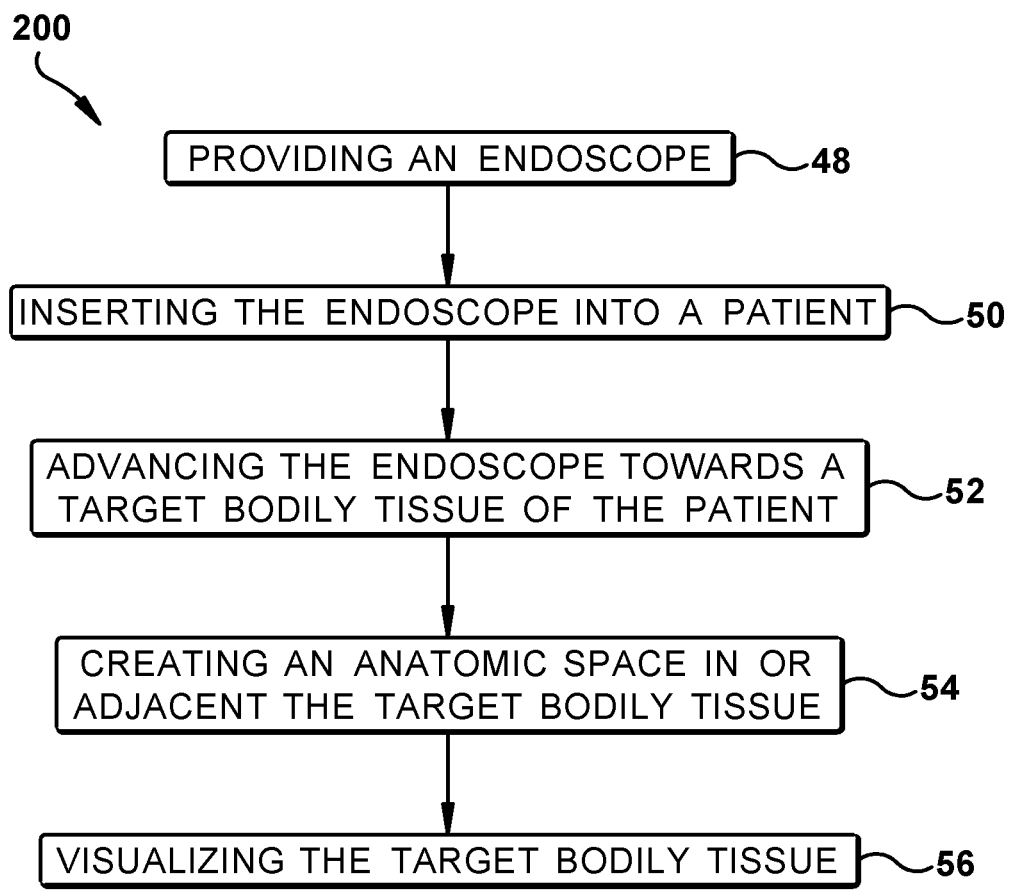
FIG. 5 is a process flow diagram illustrating a method for visualizing a target bodily tissue of a patient during a medical procedure according to another aspect of the present disclosure.

Another aspect of the present disclosure includes a method 46 (FIG. 5) for visualizing a target bodily tissue of a patient during a medical procedure. The method 46 can find use in visualizing a variety of target bodily tissues during a medical or surgical procedure, such as any transvascular, percutaneous, minimally invasive, and other less invasive medical procedure. Accordingly, a variety of target bodily tissues can be imaged including, but not limited to, digestive tract tissue, pulmonary tract tissue, cardiac tissue, muscle, tendons, cartilage, and fat tissue. As shown in FIG. 5 and described in more detail below, the method 46 of the present disclosure can generally include the following steps: providing an endoscope 10 or 10' (Step 48); inserting the endoscope into a patient (Step 50); advancing the endoscope towards a target bodily tissue of the patient (Step 52); creating an anatomic space in or adjacent the target bodily tissue (Step 54); and visualizing the target bodily tissue (Step 56).

Step 48 of the method 46 can include providing an endoscope 10 or 10'. Depending upon the particular application (e.g., the target bodily tissue to be imaged), an endoscope 10 or 10' as shown in FIGS. 1A-C or FIGS. 4A-B (respectively) can be used. Also depending upon the particular application, the dimensions of the endoscope 10 or 10' can be tailored accordingly. For example, an expandable dissecting member 14 having of a relatively small size can be selected where the target bodily tissue is located in an area constrained by surrounding anatomical structures (e.g., bones). Additionally, the endoscope 10' shown in FIGS. 4A-B may be selected for use where delivery of instruments, fluids, etc. is not required. For illustrative purposes only, the method 46 will be described using the endoscope 10 of FIGS. 1A-C.

Once a suitable endoscope 10 has been selected, the endoscope can be inserted into the patient (Step 50). The insertion point for the endoscope 10 will depend upon the particular target bodily tissue to be imaged, as well as other factors, such as the age and health of the patient. The endoscope 10 can be inserted into the patient with the expandable dissecting member 14 in the collapsed or deflated configuration. In one example, the distal end 16 of the elongate tubular member 12 can be inserted into an oral or nasal airway of the patient. In another example, the distal end 16 of the elongate tubular member 12 can be inserted into a blood vessel of the patient. In yet another example, the distal end 16 of the elongate tubular member 12 can be percutaneously inserted into a tissue (e.g., fat or muscle) of the patient. It will be appreciated that the endoscope 10 can be inserted using conventional image guidance modalities and/or under local or general anesthesia.

At Step 52, the distal end 16 of the elongate tubular member 12 can be advanced (e.g., under tactile or robotic control) towards the target bodily tissue. For example, the distal end 16 of the elongate tubular member 12 can be advanced immediately adjacent to, or into direct contact with, the target bodily tissue. Once the distal end 16 is appropriately positioned in or about the target bodily tissue, an inflation medium (e.g., air or saline) can be delivered to the interior chamber 40 of the expandable dissecting member 14 (Step 54). As the inflation medium is delivered to the interior chamber 40, the radius of expandable dissecting member 14 can increase such that the outer surface of the dissecting member generally applies forces perpendicular to the bodily tissue overlying the dissecting member. The perpendicular forces, in turn, can displace the surrounding bodily tissue and create an anatomic space. Consequently, the created anatomic space can provide an increased depth of field for endoscopic viewing. Depending upon the desired field of view, the size of the expandable dissecting member 14 can be adjusted by increasing or decreasing the amount of inflation medium delivered to the interior chamber 40.

With the dissecting member 14 in the expanded or enlarged configuration, the visualization system can then be operated to convey one or more images of the target bodily tissue from the distal end 16 of the elongate tubular member 12 to the user. Direct visualization provided by the endoscope 10 allows the user to easily view anatomic landmarks and structures. If desired, the user can perform a procedure on the target bodily tissue by, for example, advancing a surgical tool through a working channel of the elongate tubular member 12, delivering a therapeutic fluid through the central lumen 30 of the elongate tubular member, or removing a bodily fluid through the central lumen. Advantageously, the method 46 permits a user to directly visualize a target bodily tissue without the need to dissect surrounding tissue using potentially harmful gases, such as carbon dioxide. Consequently, the risk of embolism during and after the medical procedure is eliminated by the method.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. An endoscope for facilitating a medical procedure by creating an anatomic space in or adjacent a target bodily tissue to be imaged, the endoscope comprising:
   a flexible, elongate tubular member having a distal end, an inner circumferential surface, an outer circumferential surface and a central lumen extending within the inner circumferential surface, the central lumen extending coaxially with a central longitudinal axis of the elongate tubular member, the tubular member further including a plurality of imaging channels extending longitudinally therethrough, each of the imaging channels including at least a portion of a visualization system for conveying an image from the distal end of the tubular member to a user, wherein a wall of the tubular member is defined by the inner circumferential surface and the outer circumferential surface, and wherein the imaging channels are embedded within the wall and are circumferentially disposed about the central lumen; and
   an expandable dissecting member coupled to the distal end of the tubular member, the expandable dissecting member defining a channel in fluid communication with the central lumen of the tubular member, wherein the distal end of the elongate tubular member is axially spaced apart from and not flush with an opening of the channel of the expandable dissecting member located at the distal end portion of the expandable dissecting member;
   wherein a distal end portion of the expandable dissecting member obtains a toroidal shape when the expandable dissecting member is expanded such that the distal end portion encircles, and overhangs, the distal end of the elongate tubular member; and
   wherein positioning of at least one of the imaging channels being configured so that a total field of view of the visualization system does not include a distal portion of the expandable dissecting member when the expandable dissecting member is expanded.

2. The endoscope of claim 1, wherein the expandable dissecting member is designed to not be removable from the distal end of the tubular member.

3. The endoscope of claim 1, wherein the expandable dissecting member is a compliant balloon.

4. The endoscope of claim 1, wherein the plurality of imaging channels at least comprises first and second imaging channels and wherein the visualization system further comprises:

an imaging element disposed within the first imaging channel; and a lighting element disposed within the second imaging channel;

wherein each of the first and second imaging channels is disposed circumferentially about the central lumen of the tubular member.

5. The endoscope of claim 4, wherein the imaging element is an optical fiber.

6. The endoscope of claim 4, wherein the lighting element comprises a structure selected from the group consisting of an incandescent light source, a light-emitting diode, and an optical fiber.

7. The endoscope of claim 1, wherein the distal end portion of the expandable dissecting member forms a concave surface out of which the field of view of the visualization system extends distally.

8. The endoscope of claim 1, being a microendoscope.

9. The endoscope of claim 1, wherein a diameter of the central lumen is larger than diameters of the imaging channels.

10. The endoscope of claim 1, wherein the imaging channels are spaced circumferentially about the central lumen, the imaging channels being spaced evenly relative to one another in a circumferential direction.

* * * * *